United States Patent [19]

Lieber et al.

[11] 4,155,009
[45] May 15, 1979

[54] THICKNESS MEASUREMENT INSTRUMENT WITH MEMORY STORAGE OF MULTIPLE CALIBRATIONS

[75] Inventors: Sidney Lieber, Kings Point; Julius Schlesinger, Deer Park; Derek Lieber, North Merrick; Alfred Baker, Plainview, all of N.Y.

[73] Assignee: Unit Process Assemblies, Inc., Syosset, N.Y.

[21] Appl. No.: 785,530

[22] Filed: Apr. 7, 1977

[51] Int. Cl.² ............... G01N 23/00; G01D 18/00
[52] U.S. Cl. ............................ 250/308; 250/252
[58] Field of Search .................. 250/252, 308, 358

[56] References Cited

U.S. PATENT DOCUMENTS

| | | | |
|---|---|---|---|
| 3,854,042 | 12/1974 | Ott | 250/308 |
| 4,047,029 | 9/1977 | Allport | 250/358 R |

Primary Examiner—Alfred E. Smith
Assistant Examiner—Janice A. Howell

[57] ABSTRACT

An improved backscatter instrument for the nondestructive measurement of coatings on a substrate. A memory having selectable memory areas, each area having stored intelligence available which is determinative of the shape of a functional plot of coating thickness versus backscatter counts per minute unique for each particular combination of emitting isotope, substrate material, coating material and physical characteristics of the measuring instrument. A memory selector switch connects a selected area of memory to a microprocessor operating under program control whereby the microprocessor reads the intelligence stored at the selected area and converts the backscattered count of the coating being measured into indicia of coating thickness.

17 Claims, 2 Drawing Figures

THICKNESS MEASUREMENT INSTRUMENT WITH MEMORY STORAGE OF MULTIPLE CALIBRATIONS

BACKGROUND OF INVENTION

This invention relates to a backscatter thickness measuring instrument and particularly to a direct digital readout automated instrument for the non-destructive measurement of a coating on a substrate which is conditioned or calibrated by computed numerical constants stored in an internal electronic memory.

Backscatter instruments are used to measure thicknesses of coatings by counting particles backscattered from the coatings on a substrate. To determine the thickness of the coating, a user compares the normalized backscatter counts per minute with a plot of coating thickness versus normalized backscattered counts per minute. This plot, which is obtained by fitting a mathematical curve to actual normalized counts of particles backscattered from standards of known thickness, is a non-linear relationship and is unique for each combination of (1) radioactive isotope, (2) coating material, (3) substrate material and (4) the geometry of the measurement situs such as the size of aperture through which the backscattered particles must pass to reach a Geiger counter which counts the backscattered radiation. Hereafter all of these factors which are determinative of the shape of the plot shall be referred to as the "measurement parameters."

It is known in the art that when this non-linear relationship is plotted on semi-logarithmic coordinates (logarithm of thickness versus normalized counts per minute), the plot has one inflection point. For example, see FIG. 1 and 2 of U.S. Pat. No. 3,854,042 which show the general shape of curves of this type. Once the particular semi-logarithmic plot corresponding to a particular combination of measurement parameters is known, it can be defined by two curve constants denoted hereinafter by "A" and "B." The constants "A" and "B" refer to the thickness value at the inflection point on the semi-logarithmic plot and the slope of the curve at the inflection point respectively.

U.S. Pat. No. 3,271,572 disclosed a system that was adapted to provide a direct indication of the coating thickness from the beta particles backscattered from the workpiece to be measured. A meter directly responsive to the beta particles backscattered from the workpiece provided an indication of coating thickness on a readout scale calibrated to conform to the plot of thickness versus normalized beta particle back-scatter counts per minute for the particular measurement parameters. With different measurement parameters the readout scale would be replaced with a readout scale conforming to the new measurement parameters.

U.S. Patent application Ser. No. 631,412 now U.S. Pat. No. 4,079,237, filed Nov. 12, 1975 is an improvement over the system described in U.S. Pat. No. 3,271,572. This improved apparatus provides for a card controlled direct digital readout apparatus for automatically displaying the thickness of coatings. To calibrate this system for different measurement parameters, a card having the calibrating information thereon is read into the system by a card reader. In using this system a card having the calibrating information must be read each time a measurement is made.

A disadvantage of the prior art systems is that the user must calibrate the measuring apparatus each time a measurement is made. With the meter system, the readout scale must be changed for different measurement parameters, and with the card system the appropriate card must be placed in the card reader. In other systems, such as that disclosed in U.S. Pat. No. 3,854,042, calibrating information is entered into the system by dials. User error is introduced, because this calibration information must be determined by the user from tables or otherwise each time a measurement is made.

SUMMARY OF THE INVENTION

The present invention overcomes the disadvantages of known instruments for measuring the thickness of coatings by providing apparatus for automatically calculating the constants "A" and "B" and storing these in a selectable area of an electronic memory for future use when a measurement subject to the same measurement parameters is being made of a workpiece.

Considering the "A" and "B" constants for a particular combination of measurement parameters as a set, the present invention has the capability of storing multiple sets of these constants. The user simply determines which measurement parameters apply to the measurement being taken, and selects the appropriate position of a multiple position switch, each position corresponding to a particular combination of measurement parameters, whereby the "A" and "B" constants are automatically available for use by the system.

BRIEF DESCRIPTION OF THE DRAWING

In order that the invention may be clearly understood and readily carried into effect, a preferred embodiment will now be described, by way of example only, with reference to the accompanying drawings wherein.

DESCRIPTION OF A PREFERRED EMBODIMENT

Figure 1:
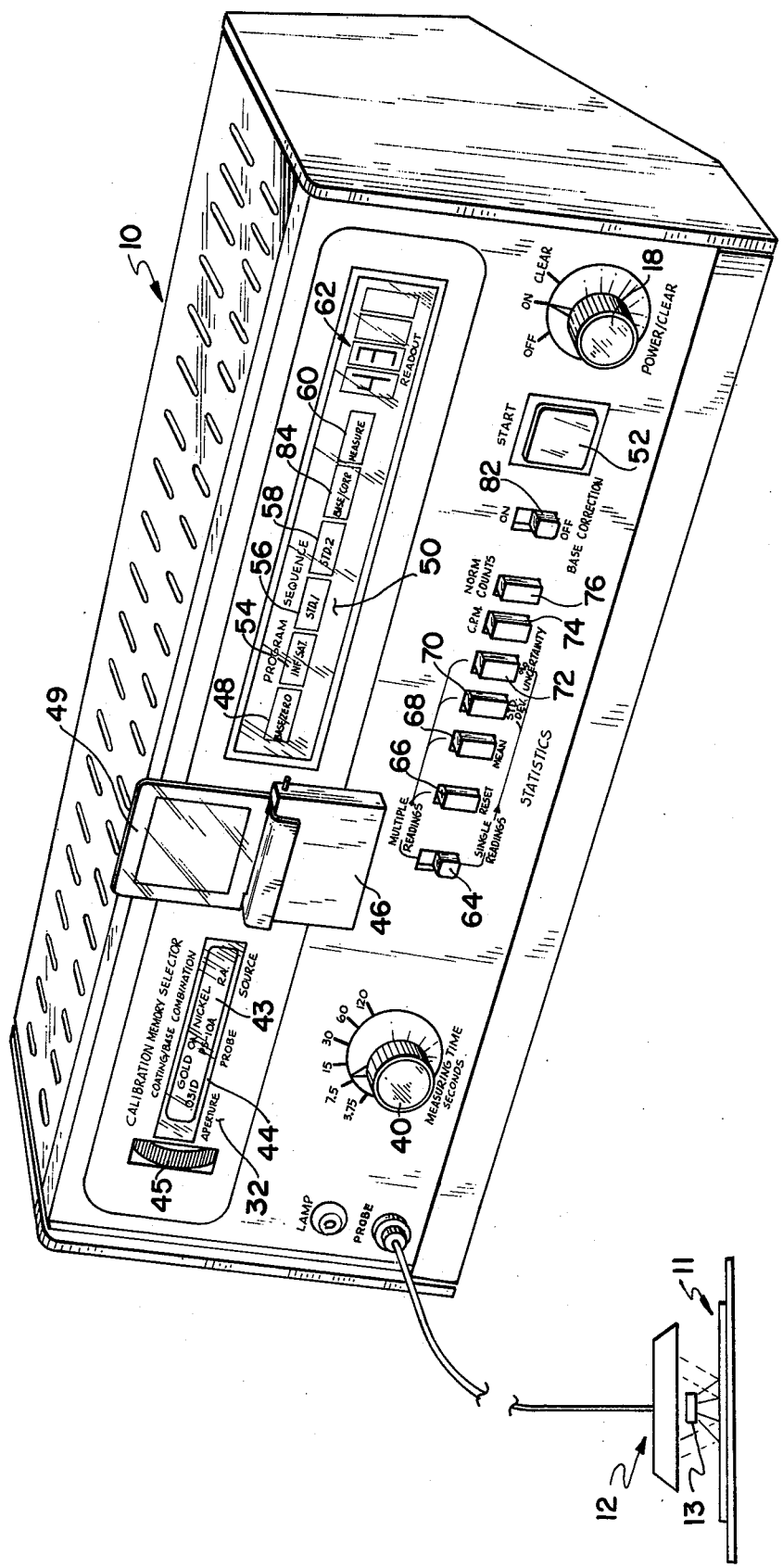
FIG. 1 is a perspective view of an apparatus according to the present invention.

In the embodiment illustrated in FIG. 1, apparatus 10 is shown for measuring and displaying the thickness of coatings on a substrate.

The apparatus 10 utilizes a probe 12 to count the backscattered radiation from the surface of a workpiece 11 being measured to determine the coating thickness. Beta particles are emitted from a radioactive isotope source 13 to irradiate the sample being measured. The backscattered beta particles are reflected through an aperture (not shown) of a Geiger counter (not shown) in the probe 12. These backscattered beta particles are converted into electrical pulses which are counted and which provide a basis for determining the thickness of the coating as described below in greater detail.

Figure 2:
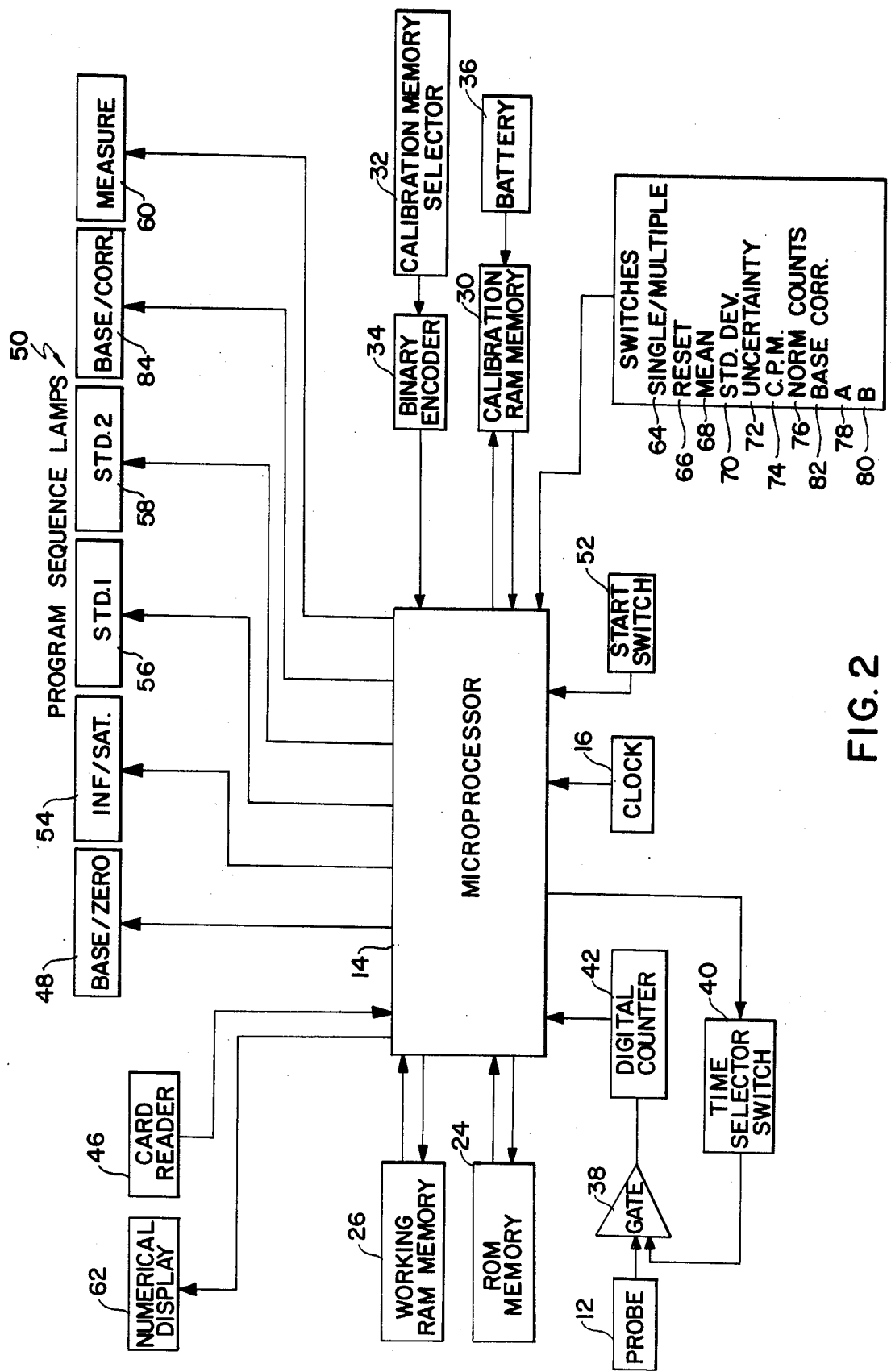
FIG. 2 is a block diagram of the major components of the apparatus illustrated in FIG. 1.

Referring to FIG. 2 a block diagram shows the major components of apparatus 10. Microprocessor 14 is a digital type processor operating under program control which is coordinated by clock 16 as is well known in the art of digital computers. A switch 18 (see FIG. 1) is movable from an off position to an on position. When moved to this on position switch 18 connects a power supply (not shown) with a line voltage source (not shown), to provide electrical power to apparatus 10.

Switch 18 also has a clear position whereby a user may reset a program counter (not shown) within the microprocessor 14 for initiating a program cycle. To clear the system a user manually moves switch 18 to the clear position. When the user releases switch 18 it moves automatically back to the on position. A working RAM memory 26 is a conventional random access memory which is used here as a working memory during the operation of microprocessor 14. A ROM memory 24 which is a conventional read only memory, permanently stores the software program for controlling the operation of the microprocessor 14. ROM memory 24 does not require outside electrical power for storing this software program, thus even in situations where the line voltage is terminated or decreased, the stored program in ROM memory 24 is not lost.

A calibration RAM memory 30 is provided for storing multiple sets of the "A" and "B" constants. The calibration RAM memory 30 may be a conventional random access memory having a number of selectable areas. The user selects one of these areas with calibration memory selector 32 which typically is of a drum type having 15 selectable positions. A binary encoder 34 creates a binary signal corresponding to the digital address of the area selected. Microprocessor 14 under program control polls the binary encoder 34 thereby determining the address of the area in calibration RAM memory 30 where the "A" and "B" constants are stored. Microprocessor 14 is now enabled to access the appropriate area in calibration RAM memory 30 either to write the "A" and "B" constants or read the "A" and "B" constants from calibration RAM memory 30. A long life battery 36 connected to the calibration RAM memory 30 maintains the stored information in calibration RAM memory 30 even when the electrical power is no longer being supplied by the power supply, for example, when switch 18 is turned to the off position.

The electrical pulsed output of probe 12 is directed to probe AND gate 38 which provides an output signal when a signal is provided on all inputs. Probe AND gate 38 has two inputs, one from probe 12 and the other from time selector switch 40 which is connected to the microprocessor 14. Time selector switch 40 is used to set the time interval during which measurements are to be made of the beta particle backscatter count from a workpiece. Time selector switch 40, under control of the programmed microprocessor 14 provides an output signal having a duration equal to the time interval selected (except when calibration measurements are made as explained below). During measurements of beta particle backscatter count from a workpiece, the probe AND gate 38 provides a pulsed output corresponding to the beta particles backscattered from the workpiece during the time interval selected on time selector switch 40. A digital counter 42 counts the pulses transmitted by probe AND gate 38 and thereby counts the particles backscattered during the time interval selected on time selector switch 40. The digital counter 42 is reset to zero under control of the program stored in ROM memory 24 prior to making a new measurement.

As previously discussed, the two constants "A" and "B" must be known before a determination can be made of the thickness of coatings when using apparatus 10. These two constants define which plot from a family of plots most clearly defines the functional relationship between coating thickness and normalized beta particle backscatter counts per minute under the conditions defined by the measurement parameters.

In the present embodiment of this invention the "A" and "B" constants need be calculated only once for a given set of particular measurement parameters. After these constants have been calculated, the microprocessor 14, under program control, replaces the constants, if any, stored in the selected area of calibration RAM memory 30 with the newly calculated constants.

Typically, calibration memory selector 32 has 15 selectable positions; therefore, 15 sets of the "A" and "B" constants can be stored corresponding to 15 different combinations of the measurement parameters. Once the constants have been stored in calibration RAM memory 30, it is unnecessary for apparatus 10 to make these calculations again. The user simply turns the drum type calibration memory selector 32 to the position corresponding to the area in calibration RAM memory 30 where the appropriate "A" and "B" constants are stored, and the microprocessor 14 under control of the program stored in ROM memory 24 accesses the particular area of memory selected and reads the values of the "A" and "B" constants previously stored. To aid the user in selecting the proper position of calibration memory selector 32, the user may write the measurement parameters on a piece of paper 43 (see FIG. 1) positioned and held around the drum of calibration memory selector 32. These measurement parameters appear in a window 44 (see FIG. 1) as the user rotates the calibration memory selector 32 by knurled knob 45.

The microprocessor 14 under control of the program stored in ROM memory 24 calculates the "A" and "B" constants according to the following equations:

$$B = \frac{\ln(T_2/T_1)}{\ln\left(\frac{\ln(1-X_2)}{\ln(1-X_1)}\right)} \quad (1)$$

$$A = \frac{T_1}{\left[\ln\left(\frac{1}{1-X_1}\right)\right]^B} \quad (2)$$

where
$T_1$ = First standard thickness of coating on substrate.
$T_2$ = Second standard thickness of coating on substrate.
$X_1$ = Normalized counts per minute for first standard.
$X_2$ = Normalized counts per minute for second standard.
ln = natural logarithm.

Normalized counts are obtained according to the following equation:

$$X = \frac{C_a - C_o}{C_s - C_o} \quad (3)$$

where
X = Normalized counts per minute.
$C_a$ = Actual counts per minute of measurement taken.
$C_o$ = Actual counts per minute where coating thickness is zero, that is the given substrate only.
$C_s$ = Actual counts per minute where coating thickness is infinity.

It can be seen that in order to calculate constants "A" and "B" the following must be known: (1) thickness of first standard (which is commonly chosen to be less than the thickness at the inflection point on the thickness versus normalized count plot): (2) thickness of a second standard (which is commonly chosen to be more than the thickness at the inflection point on the thickness versus normalized count plot); (3) counts per minute for substrate alone; (4) counts per minute for a thick coating (chosen to have a thickness such that the beta particles can no longer penetrate the coating); (5)

counts per minute for substrate with coating having a thickness of the first standard; and (6) counts per minute for substrate with coating having thickness of the second standard.

The above numerical items are entered into microprocessor 14 under program control as described below.

The user must decide on the measurement parameters defining the measurement to be taken. A card 49 typically of the type described in U.S. patent application Ser. No. 631,376 filed Nov. 12, 1975 is selected on which are encoded the values of $T_1$, the thickness of the first standard, and $T_2$, the thickness of the second standard. The user selects the card 49 in accordance with the measurement to be made and places the card 49 in card reader 46 of the type described in U.S. patent application Ser. No. 631,376. The card reader reads the encoded information on the card 49 under control of the microprocessor 14.

Microprocessor 14 polls the card reader 46 to determine whether a card 49 is present. If a card 49 is present, the microprocessor 14 under control of the program stored in ROM memory 24 enters a subroutine to calculate constants "A" and "B." If no card 49 is present in card reader 46, the microprocessor 14 under control of the program in ROM memory 24 bypasses this subroutine and enters a subroutine where the microprocessor 14 reads the address of the stored constants in calibration RAM memory 30 from the binary encoder 34 and then reads the constants "A" and "B" from the area in the calibration RAM memory 30 which has been selected by the user with calibration memory selector 32.

If the constants "A" and "B" are to be calculated, the microprocessor 14 turns on the base/zero indicator lamp 48 of the program sequence display 50 to indicate to the user that a probe 12 having a geometry and isotope source consistent with the measurement parameters already decided upon, must be positioned over a piece of substrate material which is identical to the substrate material of the workpiece to be measured.

Start switch 52 which is spring biased open is depressed to close the switch. By depressing start switch 52 the digital counter 42 is signaled to begin counting the number of backscattered beta particles during 4 times the time interval selected by the user with the time selector switch 40 and signals the microprocessor 14 to read the total count from the digital counter 42. This count is converted to counts per minute. Thus the beta particle backscattered counts per minute for the substrate only, that is $C_o$ in equation (3), is determined. This count is stored in working RAM memory 26 and a "O" is displayed on a numerical display 62 which typically is a binary coded decimal display device of conventional construction to indicate that the counts per minute of backscattered beta particles for the substrate only has been determined.

After the substrate only count has been stored, microprocessor 14 turns the Base/Zero lamp 48 off and the Inf./Sat. lamp 54 on to indicate to the user that the probe 12 must be positioned over a thick piece of coating material having a thickness which the beta particles can not penetrate. The abbreviation Inf./Sat. when used with lamp 54 means that the coating material is thick (quasi-infinite) and that the measurement made will be at saturation. This coating material is identical to the coating material of the workpiece to be measured. After the probe 12 is positioned, the start switch 52 is depressed and the digital counter 42 counts the beta particle backscattered count during 4 times the time interval selected on time selector switch 40. Microprocessor 14 then reads this count, converts this count to counts per minute, stores this count in an area of the working RAM memory 26 and displays a "SA" on numerical display 62 to indicate that the measurement of the counts per minute of the backscattered beta particles from the thick piece of coating material has been completed. Thus the counts per minute for a thick quasi-infinite coating on the substrate is known and stored. This count is the $C_s$ in equation (3).

Next, the microprocessor 14 under program control turns the Inf./Sat. lamp 54 off and turns the Std. 1 lamp 56 on. This indicates to the user to position the probe 12 on a substrate piece with a layer of coating material having the first standard thickness corresponding to $T_1$ encoded on card 49 in card reader 46. After positioning the probe 12 the start switch 52 is depressed and the beta backscatter counts per minute is determined and stored as before in working RAM memory 26. The microprocessor 14 under program control normalizes this count according to equation (3) and stores this normalized count in working RAM memory 26. This normalized count is $X_1$ in equations (1) and (2). Microprocessor 14 displays the value of $T_1$ on numerical display 62 to indicate to the user that the measurement of the counts per minute for first standard has been completed.

Next, the microprocessor 14 under program control turns the Std. 1 lamp 56 off and turns the Std. 2 lamp 58 on. This indicates to the user that the probe 12 must be positioned over a substrate piece with a layer of coating having the second standard thickness corresonding to $T_2$ encoded on card 49 in card reader 46. The user depresses start switch 52. The beta particle backscatter counts per minute is determined and stored in working RAM memory 26. The microprocessor 14 under program control normalizes this count according to equation (3) and stores this normalized count in working RAM memory 26. This normalized count is $X_2$ in equation (1). Microprocessor 14 displays the value of $T_2$ on numerical display 62 to indicate to the user that the measurement of the counts per minute for the second standard has been completed.

The microprocessor 14 under program control can now determine the "A" and "B" constants defining the non-linear relationship between normalized beta particle back-scatter counts per minute and thickness according to equations (1) and (2).

After the constants have been calculated the microprocessor 14 under program control replaces the constants, if any, stored in the selected area of calibration RAM memory 30 with the calculated constants. These newly stored constants can now be recalled for future measurements of workpieces if the measurement parameters are the same as when these constants were determined.

The calibration of apparatus 10 for the measurement parameters decided upon is completed when the "A" and "B" constants corresponding to these measurement parameters are stored in calibration RAM memory 30 and the backscattered counts per minute corresponding to $C_o$ and $C_s$ are stored in working RAM memory 26. After calibration, apparatus 10 may be used to measure and display the coating thickness of a workpiece having unknown coating thickness. The Std. 2 lamp 58 is turned off by microprocessor 14 and the Measure lamp 60 is turned on. This indicates to the user that probe 12 may be positioned on the workpiece having unknown coating thickness. The user then depresses start switch 52 and the microprocessor 14 determines the beta particle backscatter count from the digital counter 42 for the time selected on the time selector switch 40. Microprocessor 14 under control of the program then converts this count to normalized counts per minute and calculates the thickness of the coating according to the following formula:

$$T = A\left(\ln\left(\frac{1}{1-X}\right)\right)^B \quad (4)$$

where
- T = Thickness
- A = "A" Constant
- B = "B" Constant
- X = Normalized backscattered beta particle counts per minute
- ln = natural logarithm The thickness is then displayed under control of the microprocessor 14 on numerical display 62.

Since $C_o$ and C and the "A" and "B" constants are now available for use by microprocessor 14, the apparatus 10 is fully calibrated for the measurement parameters previously decided upon; and a thickness measurement may be made of a coating on any workpiece having substrate material and coating material consistent with the measurement parameters. In measuring the thickness of such a workpiece it is not necessary to redetermine $C_o$ and $C_s$. Microprocessor 14, under program control, automatically turns the Measure lamp 60 on to indicate to the user that probe 12 must be positioned over the workpiece to be measured. After positioning probe 12 and depressing start switch 52, the thickness of the coating is calculated by microprocessor 14 and displayed on numerical display 62 as previously described.

Apparatus 10 may also be used to calculate a mean of a series of measurements and to calculate the standard deviation and percent uncertainty of this series of measurements. A user may select any of these operations by feature switches located on the front panel of apparatus 10 (see FIG. 1). These include a single/multiple switch 64 slidable from a first position to a second position and several push button switches including mean switch 68, Std. Dev. switch 70 and uncertainty switch 72, which are spring biased open but may be depressed by the user to close the switch. All of these switches are polled by the microprocessor 14 to determine their status.

When single/multiple switch 64 is moved to the first position corresponding to a single measurement mode, the microprocessor 14 under program control simply calculates the thickness of a measurement according to equation (4) and displays this thickness measurement on numerical display 62.

When single/multiple switch 64 is moved to the second position corresponding to a multiple measurement mode, the microprocessor 14 under program control enters a subroutine whereby successive thickness measurements are stored in working RAM memory 26. To initiate this process the user depresses start switch 52 for the first measurement and the microprocessor 14 alternately displays on numerical display 62 the thickness calculated during the first measurement and, a "1" to indicate to the user that this is the first measurement. The user then depresses start switch 52 and the microprocessor 14 alternately displays on numerical display 62 the thickness calculated during the second measurement and a "2" to indicate to the user that this is the second measurement. If the user wants to know the mean of these two measurements, the mean switch 68 is depressed and the microprocessor 14 under control of the program stored in ROM memory 24 calculates the mean of these two measurements. As long as the mean switch 68 is depressed, the value of the mean is displayed on numerical display 62. In a similar manner if the standard deviation or percent uncertainty of this series of measurements is desired, the user depresses Std. Dev. switch 70 or uncertainty switch 72 respectively. The values will be displayed only as long as the corresponding switch is depressed.

If the user decides to make more measurements, the start switch 52 is depressed and the next measurement is made. Continuing with the above example, this would be the third measurement and the thickness measurement would be alternately displayed on numerical display 62 with the number "3" to indicate that this is the third measurement. Again the means, standard deviation and percent uncertainty of the three measurements can be obtained by depressing the corresponding feature switches.

When the measurement parameters are changed, the apparatus 10 is easily recalibrated when the "A" and "B" constants are already stored in calibration RAM memory 30. In this case only $C_o$ and $C_s$ (equation (3)) need be determined. In the present embodiment these counts are determined each time the measurement parameters are changed or when the apparatus 10 has been turned off. In another embodiment described below the $C_o$ and $C_s$ values for particular measurement parameters are stored together with corresponding "A" and "B" constants in calibration RAM memory 30. Since many isotopes are subject to decay, it is common for the emission of isotope 13 to vary with age. When this is the case, the present embodiment is useful, because the emission of the particular isotope is taken into account, when calibrating the apparatus 10 through determination of $C_o$ and $C_s$ using the particular isotope.

Assuming the "A" and "B" constants for the particular measurement parameters are already stored in calibration RAM memory 30, there will be no card in card reader 46 and the program in ROM memory 24 causes microprocessor 14 to bypass the subroutine for calculating the "A" and "B" constants. The user turns calibration memory selector 32 to the position corresponding to the measurement parameters of the measurement to be made. Thus the appropriate set of "A" and "B" constants are available for use by microprocessor 14.

To determine $C_o$, the microprocessor 14 turns the Base/Zero lamp 48 on to indicate that the user must position probe 12 over a piece of substrate material of the workpiece to be measured. Start switch 52 is depressed and $C_o$ is determined and an "0" is displayed on numerical display 62 as previously described.

To determine $C_s$, the microprocessor 14 under program control then turns Base/Zero lamp 48 off and turns Inf./Sat. lamp 54 on to indicate to the user that probe 12 must be positioned over a quasi-infinite thick piece of coating material identical to the coating material of the workpiece to be measured. The user then depresses start switch 52, and $C_s$ is determined and an "SA" displayed on numerical display 62 as previously described.

Since the "A" and "B" constants are already stored in calibration RAM memory 30 and are available for use by the microprocessor 14, apparatus 10 is fully calibrated once $C_o$ and $C_s$ have been determined. Apparatus 10 may now be used to take accurate measurements of coating thickness as previously described.

Apparatus 10 under control of the program stored in ROM memory 24 has the capability of predicting an approximate value of standard deviation and percent uncertainty for a time interval selected on the time selector switch 40. It is well known that the longer the time interval over which a measurement of the backscattered beta particles is made, the more accurate the mean and the lower the value of the percent uncertainty. To make this prediction, the user selects the desired time interval on time selector switch 40, moves the single/multiple switch 64 to the first position corresponding to the single measurement mode and depresses either the Std. Dev. switch 70 or the uncertainty switch 72. When the Std. Dev. switch 70 is depressed the microprocessor 14 under program control calculates the predicted standard deviation of the last measurement taken as follows:

$$\sigma = T' - T \tag{5}$$

where
- $\sigma$ = Predicted standard deviation.
- T = The thickness of the last measurement calculated for this measurement using equation (4).

$$T' = A \left[ \ln \left[ \frac{1}{1 - \left( \frac{C_a + .00093 C_a + \frac{85}{t} - C_o}{C_s - C_o} \right)} \right] \right]^B$$

where
- $C_a$, $C_o$ and $C_s$ = The definitions set forth for equation (3).
- t = time interval (in minutes) selected with time selector switch 40.

and displays the value of the predicted standard deviation on numerical display 62.

When the uncertainty switch 72 is depressed, the microprocessor 14 under program control calculates the predicted percent uncertainty of the last measurement as follows:

$$U = 200 \frac{\sigma}{T} \tag{6}$$

where
- U = Predicted percent uncertainty for last measurement at a 95% confidence limit.
- $\sigma$ = Predicted standard deviation according to equation (5).
- T = The thickness of the last measurement calculated for this measurement using equation (4).

and displays the value of the predicted percent uncertainty on the numerical display 62.

By using this programmed feature a user may adjust the time interval with time selector switch 40 until the percent uncertainty or standard deviation reaches a desireable level. If the user were to take a series of measurements with the time selector switch 40 set to this time interval, the series of measurements at this time interval setting would have a percent uncertainty or standard deviation approximately equal to that predicted.

If the user wants to know the beta particle backscattered counts per minute for a particular measurement a C.P.M. switch 74 is closed. If the user wants to know the normalized counts per minute for a particular measurement, a Norm. Count switch 76 is closed. Furthermore, if the user wants to know the value of the "A" or "B" constants stored in calibration RAM memory 30, the user closes A switch 78 and B switch 80 respectively. These two switches are not shown on FIG. 1 because they are located on a rear panel of apparatus 10. All of these switches are spring biased open and can be closed by depressing the particular switch. Microprocessor 14 polls the switches to determine whether they are closed.

Apparatus 10 may also be calibrated to take measurements of coated substrates in which the substrate material has an atomic number slightly different from that for which "A" and "B" constants are stored in the calibration RAM memory 30. Of course, when used in this manner, the measurement parameters must otherwise be the same. The user moves a slideable Base Corr. switch 82 from a first position which corresponds to normal operation of the apparatus to a second position. The abbreviation Base. Corr. when used in conjunction with switch 82 means that a measurement is being made with a calibration adjustment for a slightly different substrate material, i.e. with a base correction. When the Base. Corr. switch 82 is moved to the second position, a Base. Corr. lamp 84 is turned on. When the Base. Corr. switch 82 is moved to the normal first position, the Base. Corr. lamp 84 is turned off. The microprocessor 14 polls this switch and if the switch is in the second position, the microprocessor 14 under program control enters a subroutine to calibrate the apparatus for this new substrate material. The microprocessor 14 approximates the proper calibration by normalizing the counts per minute according to the following equation:

$$X = \frac{C_a - C_b}{C_s - C_b} \tag{6}$$

where
- X = Normalized counts per minute
- $C_a$ = Actual counts per minute measured
- $C_b$ = Actual counts per minute for new substrate only
- $C_s$ = Actual counts per minute where coating thickness is infinity instead of using equation (3). Using this technique a user may obtain a reasonably accurate thickness measurement of a coating on a substrate when the user does not have the two thickness standards required in calculating the "A" and "B" constants according to equations (1) and (2).

In another embodiment of this invention, the "A" and "B" constants are read by the microprocessor 14 from card 49 directly. In this embodiment indicia of these constants are encoded on card 49. When this card 49 is placed in card reader 46, the microprocessor 14 is signaled to read the constants from the card and store the constants in the area in calibration RAM memory 30 as selected by the user with calibration memory selector 32. In this embodiment it is not necessary for the microprocessor 14 to calculate the "A" and "B" constants using equations (1) and (2).

In another embodiment of this invention, the "B" constant and a value of $T_1$ is read by the microprocessor 14 from card 49 directly and the "A" constant is calculated by the microprocessor 14 according to equation (2), after the value of $X_1$ is calculated as before. The values of the "A" and "B" constants are then stored in the area of calibration RAM memory 30 which the user selects with calibration memory selector 32.

In another embodiment of this invention, the count measurements $C_o$ and $C_s$ in equation (3) are stored together with the corresponding "A" and "B" constants in the selected area of calibration RAM memory 30. This embodiment is typically used when it is unnecessary to take the variation of emission of isotope 13 into account when calibrating apparatus 10. Prior to storing $C_o$ and $C_s$ these values must be determined as was done with the first embodiment. After storing $C_o$ and $C_s$ for particular measurement parameters together with the "A" and "B" constants for the measurement parameters the thickness value can be calculated according to equation (4) when the actual counts of beta particles backscattered from the workpiece is measured. Thus, when $C_o$, $C_s$, and "A" and "B" are stored, it is unnecessary to calibrate apparatus 10 to determine the thickness of a coating on a substrate. The user selects the appropriate area of calibration RAM memory 30 where this intelligence is stored, and microprocessor 14 under program control automatically enters a measurement mode of operation. Microprocessor 14 turns the Measure lamp 60 on indicating to the user that probe 12 must be positioned on the workpiece to be measured. Calculation of coating thickness is then accomplished as previously described with the first embodiment. All of the other features of the first embodiment including calculation of the mean, standard deviation, and percent uncertainty are available with this embodiment.

While the fundamental novel features of the invention have been shown and described, it should be understood that various substitutions, modifications and variations may be made by those skilled in the art without departing from the spirit or scope of the invention. Accordingly, all such modifications and variations are included in the scope of the invention as defined by the following claims.

I claim:

1. A backscatter apparatus for nondestructively measuring the thickness of a coating on a substrate comprising:
    radioactive isotope means for irradiating the coating with particles;
    means for counting backscattered particles;
    a microprocessor operating under control of a program to convert the count of backscattered particles into indicia of coating thickness in accordance with a functional relationship between thickness and count of backscattered particles per minute for a given isotope, given substrate material, given coating material and given geometry of a measurement situs;
    a memory means having multiple selectable areas, each area having available stored intelligence of a particular functional relationship in a format readable by the microprocessor;
    means for selecting an area in memory; and
    means responsive to the selecting means for connecting the selected area in memory to the microprocessor whereby when so connected the microprocessor under program control reads the intelligence stored at the selected area in memory and makes the conversion in accordance with this intelligence.

2. The backscatter apparatus according to claim 1 wherein the radioactive isotope irradiates the coating with beta particles.

3. The backscatter apparatus according to claim 2 wherein the intelligence determinative of the functional relationship between thickness and count of backscattered beta particles per minute are numerical constants and including:
    a control card having indicia of at least one standard thickness of the given coating material and wherein the microprocessor is conditioned by the indicia on the control card to calculate the numerical constants in accord with the indicia of standard thickness and to replace the intelligence in the selected area with the calculated numerical constants.

4. The backscatter apparatus according to claim 1 wherein the indicia of coating thickness are binary in format and further including a digital display means responsive to the indica of coating thickness for displaying coating thickness.

5. The backscatter apparatus according to claim 1 further including:
    switching means for switching from a first position corresponding to making a single measurement to a second position corresponding to making successive measurements of the thickness of a coating on a substrate; and
    working means for storing intelligence; and wherein the microprocessor under program control is connected to the working memory means and stores a series of successive measurements of the thickness of coating in the working memory means when the switching means is switched to the second position until the switching means is switched to the first position; and further including:
    means for selectively conditioning the microprocessor to calculate the value of mean thickness of the coating for the series of successive measurements; and
    means for displaying the value of mean thickness.

6. The backscatter apparatus according to claim 5 further including:
    means for selectively conditioning the microprocessor to calculate a value of standard deviation of the series of successive measurements; and
    means for displaying the value of standard deviation.

7. The backscatter apparatus according to claim 5 further including:
    means for selectively conditioning the microprocessor to calculate a value of percent uncertainty of the series of successive measurements; and
    means for displaying the value of percent uncertainty.

8. The backscatter apparatus according to claim 5 further including:
    timer means for selecting a time interval; and wherein the counting means is selectively activated to count backscattered particles for the selected time interval when a measurement is taken and further including:
    means for selectively conditioning the microprocessor to calculate a predicted value of standard deviation for this measurement, when the switching means is switched to the first position, for any time interval selected with timer means after the measurement is taken.

9. The backscatter apparatus according to claim 5 further including:
  timer means for selecting a time inverval, and wherein the counting means is selectively activated to count backscattered particles for the selected time interval when a measurement is taken and further including:
  means for selectively conditioning the microprocessor to calculate a predicted value of percent uncertainty for this measurement, when the switching means is switched to the first position, for any time interval selected with timer means after the measurement is taken.

10. The backscatter apparatus according to claim 1 wherein the intelligence determinative of the functional relationship between thickness and count of backscattered beta particles per minute are numerical constants and further including:
  a control card having indicia of predetermined numerical constants;
and wherein the microprocessor is conditioned by the indicia of the predetermined numerical constants on the control card to replace intelligence in the selected area in memory with such predetermined numerical constants.

11. The backscatter apparatus according to claim 1 wherein the intelligence determinative of the functional relationship between thickness and count of backscattered beta particles per minute are numerical constants and including:
  a control card having indicia of a predetermined standard thickness and a predetermined numerical constant;
  and wherein the microprocessor is conditioned by the indicia on the control card to calculate other numerical constants and to replace the intelligence in the selected area with the predetermined numerical constants on the control card and the calculated numerical constants.

12. The backscatter apparatus according to claim 1 wherein the stored intelligence determinative of the functional relationship between thickness and count of backscattered particles per minute includes normalization data.

13. A method for non-destructively measuring the thickness of a coating on a substrate using beta particle backscattering techniques comprising:
  irradiating the coating with particles from a radioactive isotope;
  counting the particles backscattered from the coating and substrate;
  selecting an area in a memory means having multiple selectable areas, each area having available stored intelligence of a functional relationship between thickness and count of backscattered particles per minute for a given isotope, given substrate material, given coating material and given geometry of a measurement situs; and
  converting the count of backscattered particles into indicia of coating thickness in accordance with the intelligence of the functional relationship stored at the selected area in memory.

14. The method of claim 13, wherein the intelligence determinative of the functional relationship between thickness and count of backscattered particles per minute are numerical constants and further including the steps of:
  reading encoded indicia of at least one standard thickness of the given coating material from a control card;
  calculating the numerical constants in accord with the indicia of standard thickness; and
  replacing the intelligence stored in the selected area in the memory means with the calculated numerical constants.

15. The method of claim 13 wherein the intelligence determinative of the functional relationship between thickness and count of backscattered particles per minute are numerical constants and further including the steps of:
  reading encoded indicia of predetermined numerical constants from a control card; and
  replacing the intelligence stored in the selected area in the memory means with the predetermined numerical constants read from the control card.

16. The method of claim 13 wherein the intelligence determinative of the functional relationship between thickness and count of backscattered particles per minute are numerical constants and further including the steps of:
  reading encoded indicia of a predetermined standard thickness and a predetermined numerical constant from a control card;
  calculating other numerical constants in accord with the indicia of the predetermined standard thickness and the indicia of the predetermined numerical constant read from the control card; and
  replacing the intelligence stored in the selected area in memory means with the predetermined numerical constant read from the control card and the calculated numerical constants.

17. The method of claim 13 wherein the intelligence determinative of the functional relationship between thickness and count of backscattered particles per minute includes normalization data.

* * * * *